US00PP29901P3

(12) United States Plant Patent
Wain

(10) Patent No.: US PP29,901 P3
(45) Date of Patent: Nov. 27, 2018

(54) ***CHRYSANTHEMUM* PLANT NAMED 'FICHRYCOSYEL'**

(50) Latin Name: *Chrysanthemum X morifolium*
Varietal Denomination: Fichrycosyel

(71) Applicant: DUMMEN GROUP B.V., De Lier (NL)

(72) Inventor: Peter Wain, Locks Heath (GB)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/732,508

(22) Filed: Nov. 21, 2017

(65) Prior Publication Data

US 2018/0146597 P1 May 24, 2018

Related U.S. Application Data

(60) Provisional application No. 62/497,574, filed on Nov. 22, 2016.

(51) Int. Cl.
*A01H 5/02* (2018.01)
*A01H 6/14* (2018.01)

(52) U.S. Cl.
USPC ..... Plt./289
CPC ..... *A01H 6/1424* (2018.05); *A01H 5/02* (2013.01); *A01H 5/0255* (2013.01)

(58) Field of Classification Search
USPC ..... Plt./289
CPC ..... A01H 5/0255
See application file for complete search history.

*Primary Examiner* — Kent L Bell
(74) *Attorney, Agent, or Firm* — C. A. Whealy

(57) ABSTRACT

A new and distinct cultivar of *Chrysanthemum* plant named 'Fichrycosyel', characterized by its relatively compact, upright and uniformly mounded plant habit; moderately vigorous growth habit; uniform flowering habit; large incurved decorative-type inflorescences with yellow-colored ray florets; response time about 56 days under controlled photoperiodic treatments; and good postproduction longevity.

1 Drawing Sheet

Botanical designation: *Chrysanthemum* X *morifolium*.
Cultivar denomination: 'FICHRYCOSYEL'.

CROSS-REFERENCED TO CLOSELY RELATED APPLICATION

Title: *Chrysanthemum* Plant Named 'Fichrycoswhi'
Applicant: Peter Wain
Filed: Concurrently with this application U.S. Plant patent application Ser. No. 15/732,509

BACKGROUND OF THE INVENTION

The present invention relates to a new and distinct *Chrysanthemum* plant, botanically known as *Chrysanthemum* X *morifolium*, commercially grown as a disbudded potted *Chrysanthemum* plant and hereinafter referred to by the name 'Fichrycosyel'.

The new *Chrysanthemum* plant is a product of a planned breeding program conducted by the Inventor in Fareham, Hampshire, United Kingdom and De Lier, The Netherlands. The objective of the breeding program is to create new potted *Chrysanthemum* plants with large incurved decorative-type inflorescences.

The new *Chrysanthemum* plant is a naturally-occurring whole plant mutation of *Chrysanthemum* X *morifolium* 'Fichrycospur', disclosed in U.S. Plant patent application Ser. No. 15/732,509. The new *Chrysanthemum* plant was discovered and selected by the Inventor as a single flowering plant from within a population of plants of 'Fichrycospur' in a controlled greenhouse environment in De Lier, The Netherlands during the spring of 2014.

Asexual reproduction of the new *Chrysanthemum* plant by terminal vegetative cuttings was first conducted in De Lier, The Netherlands during the spring of 2014. Asexual reproduction by terminal vegetative cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Fichrycosyel'. These characteristics in combination distinguish 'Fichrycosyel' as a new and distinct *Chrysanthemum* plant:

1. Relatively compact, upright and uniformly mounded plant habit.
2. Moderately vigorous growth habit.
3. Uniform flowering habit.
4. Large incurved decorative-type inflorescences with yellow-colored ray florets.
5. Response time about 56 days under controlled photoperiodic treatments.
6. Good postproduction longevity.

Plants of the new *Chrysanthemum* can be compared to plants of the mutation parent, 'Fichrycospur'. Plants of the new *Chrysanthemum* differ primarily from plants of 'Fichrycospur' in ray floret color as plants of 'Fichrycospur' have inflorescences with red purple-colored ray florets.

Plants of the new *Chrysanthemum* can be compared to plants of *Chrysanthemum* x *morifolium* 'Fichrycoswhi', disclosed in U.S. Plant patent application Ser. No. 15/732,509 with this application. Plants of the new *Chrysanthemum* differ primarily from plants of 'Fichrycoswhi' in ray floret color as plants of the 'Fichrycoswhi' have inflorescences with white-colored ray florets.

Plants of the new *Chrysanthemum* can be compared to plants of *Chrysanthemum* X *morifolium* 'Zembla Yellow', disclosed in U.S. Plant Pat. No. 14,733. In side-by-side comparisons, plants of the new *Chrysanthemum* differ primarily from plants of 'Zembla Yellow' in time to flower as plants of the new *Chrysanthemum* flower about four days later than plants of 'Zembla Yellow'. In addition, plants of the new *Chrysanthemum* are more compact than plants of 'Zembla Yellow'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant. The photograph is a top perspective view of a typical flowering plant of 'Fichrycosyel' grown in a 14-cm container.

DETAILED BOTANICAL DESCRIPTION

The aforementioned photograph and following observations and measurements describe plants grown during the summer in 14-cm containers in a glass-covered greenhouse in Fareham, Hampshire, United Kingdom and under cultural practices typical of commercial potted *Chrysanthemum* production. During the production of the plants, day and night temperatures ranged from 17° C. to 21° C. and light levels averaged 6,000 lux. Plants were grown under long day/short night conditions for about two weeks and then grown under short day/long night conditions to induce inflorescence initiation and development. Plants were not pinched and were ten weeks old when the photograph and detailed description were taken. In the following description, color references are made to The Royal Horticultural Society Colour Chart, Fifth Edition, except where general terms of ordinary dictionary significance are used.

Botanical classification: *Chrysanthemum* X *morifolium* 'Fichrycosyel'.

Parentage: Naturally-occurring whole plant mutation of *Chrysanthemum* X *morifolium* 'Fichrycospur', disclosed in U.S. Plant patent application Ser. No. 15/732,510.

Propagation:

*Type*.—Terminal vegetative cuttings.

*Time to initiate roots, summer*.—About ten days at temperatures about 21° C.

*Time to initiate roots, winter*.—About twelve days at temperatures about 21° C.

*Time to produce a rooted young plant, summer*.—About three weeks at temperatures about 21° C.

*Time to produce a rooted young plant, winter*.—About four weeks at temperatures about 21° C.

*Root description*.—Medium in thickness, fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous incurved decorative-type potted *Chrysanthemum*; stems upright to slightly outwardly spreading giving a uniformly mounded appearance to the plant; moderately vigorous growth habit.

*Plant height*.—About 17 cm.

*Plant width*.—About 34 cm.

*Lateral branches (peduncles)*.—Length: About 15 cm. Diameter: About 4 mm. Internode length: About 1 cm. Strength: Strong. Aspect: Mostly upright to slightly outwardly. Texture: Fine pubescence. Color: Close to 148B.

Leaf description:

*Arrangement*.—Alternate, simple.

*Length*.—About 6 cm.

*Width*.—About 4.5 cm.

*Shape*.—Palmately-lobed; roughly ovate with three to five lobes.

*Apex*.—Broadly acuminate.

*Base*.—Attenuate.

*Margin*.—Slightly dentate and palmately lobed; sinuses between lateral lobes mostly divergent.

*Texture, upper and lower surfaces*.—Fine pubescence; slightly rough; veins prominent on lower surface.

*Color*.—Developing leaves, upper surface: Close to 137B. Developing leaves, lower surface: Close to 147B. Fully expanded leaves, upper surface: Close to 137A; venation, close to 138B. Fully expanded leaves, lower surface: Close to 137C; venation, close to 138B.

*Petioles*.—Length: About 1 cm. Diameter: About 4 mm. Texture, upper and lower surfaces: Fine pubescence; slightly rough. Color, upper and lower surfaces: Close to 138B.

Inflorescence description:

*Form and flowering habit*.—Incurved decorative-type inflorescence form with ligulate-shaped ray florets; inflorescences borne on terminals above and beyond the foliar plane; ray florets arranged acropetally on a capitulum; grown as a disbud-type, only the terminal inflorescence develops.

*Fragrance*.—Mildly fragrant; pungent, herbaceous.

*Flowering response*.—Plants flower uniformly about 56 days after starting short day/long night photoperiodic treatments.

*Inflorescence longevity*.—Good postproduction longevity; inflorescences maintain good color and substance for about three to five weeks on the plant; inflorescences persistent.

*Inflorescence diameter*.—Large, about 10 cm.

*Inflorescence height*.—About 3 cm.

*Receptacles*.—Height: About 3 mm. Diameter: About 5 mm. Shape: Oblate. Color: Close to 145C.

*Ray florets*.—Number of ray florets per inflorescence: About 267 arranged in about twelve whorls. Orientation: Initially upright, then about 80° from vertical; strongly incurved. Length: About 4 cm. Width: About 1.3 cm. Shape: Ligulate. Apex: Obtuse. Base: Fused into a short tube. Margin: Entire. Texture, upper and lower surfaces: Smooth, glabrous; doublekeeled. Color: When opening, upper surface: Close to 3A. When opening, lower surface: Close to 3C. Fully opened, upper surface: Close to 8A; with development, color becoming closer to 5C. Fully opened, lower surface: Close to 8C; with development, color becoming closer to 5D.

*Disc florets*.—Disc floret initiation and development has not been observed on plants of the new *Chrysanthemum* to date.

*Phyllaries*.—Number of phyllaries per inflorescence: About 40 arranged in about three whorls. Length: About 1 cm. Width: About 5 mm. Shape: Lanceolate. Apex: Acute. Base: Obtuse. Margin: Entire. Texture, upper surface: Smooth, glabrous; waxy. Texture, lower surface: Fine pubescence; waxy. Color, upper and lower surfaces: Close to 144A.

*Reproductive organs*.—Androecium: None observed. Gynoecium: Present only on ray florets. Pistil length: About 5 mm. Stigma shape: Bi-parted. Stigma color: Close to 6B. Style length: About 0.5 mm. Style color: Close to 1C. Ovary color: Close to N155B.

*Seeds and fruits*.—Seed and fruit production has not been observed on plants of the new *Chrysanthemum* to date.

Disease & pest resistance: Resistance to pathogens and pests common to *Chrysanthemum* plants has not been observed on plants of the new *Chrysanthemum* to date.

Garden performance: Plants of the new *Chrysanthemum* have demonstrated good garden performance and to tolerate temperatures from about 0° C. to about 35° C.

It is claimed:

1. A new and distinct *Chrysanthemum* plant named 'Fichrycosyel' as illustrated and described.

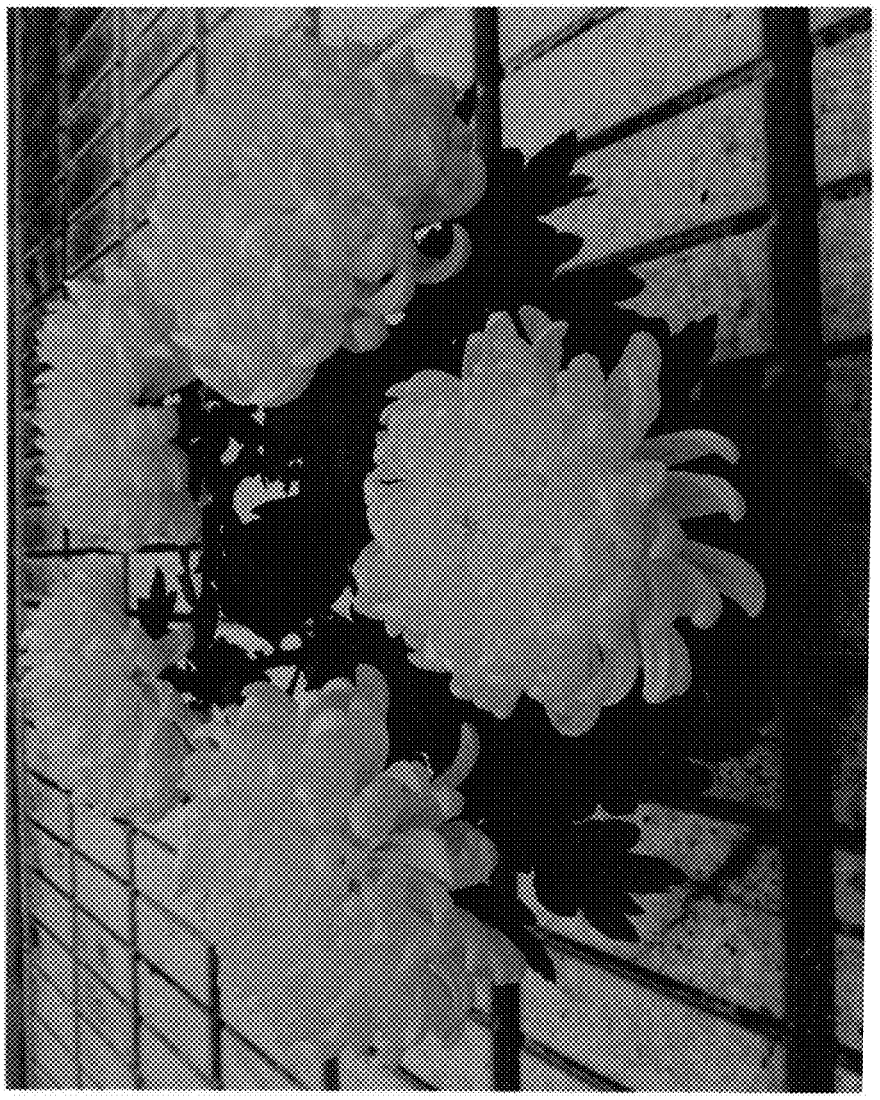

* * * * *